United States Patent [19]
Ochs et al.

[11] Patent Number: 5,899,925
[45] Date of Patent: May 4, 1999

[54] METHOD AND APPARATUS FOR APERIODIC SELF-TESTING OF A DEFIBRILLATOR

[75] Inventors: Dennis E. Ochs, Bellevue; Carlton B. Morgan, Bainbridge Island, both of Wash.

[73] Assignee: Heartstream, Inc., Seattle, Wash.

[21] Appl. No.: 08/910,970

[22] Filed: Aug. 7, 1997

[51] Int. Cl.⁶ ........................................................ A61N 1/39
[52] U.S. Cl. ............................................................... 607/5
[58] Field of Search ..................................................... 607/5

[56] References Cited

U.S. PATENT DOCUMENTS

| | | |
|---|---|---|
| 3,747,605 | 7/1973 | Cook . |
| 3,983,476 | 9/1976 | Konopasek . |
| 4,164,946 | 8/1979 | Langer . |
| 4,295,474 | 10/1981 | Fischell et al. . |
| 4,300,567 | 11/1981 | Kolenik et al. . |
| 4,353,372 | 10/1982 | Ayer . |
| 4,404,972 | 9/1983 | Gordon et al. . |
| 4,407,288 | 10/1983 | Langer et al. . |

(List continued on next page.)

FOREIGN PATENT DOCUMENTS

| | | |
|---|---|---|
| 0327304 A1 | 8/1989 | European Pat. Off. . |
| 0472411 A1 | 2/1992 | European Pat. Off. . |
| 0551746 A2 | 7/1993 | European Pat. Off. . |
| 0671687 A2 | 9/1995 | European Pat. Off. . |
| 2172681 | 9/1973 | France . |
| 2712352 A1 | 9/1978 | Germany . |
| 2272376 | 5/1994 | United Kingdom . |
| WO 93/16759 | 9/1993 | WIPO . |
| 9427674 | 12/1994 | WIPO ........................................ 607/5 |

OTHER PUBLICATIONS

Product Brochure from "Vivalink AED Automatic External Defibrillator System" by Survivalink Corporation.

*Primary Examiner*—William E. Kamm
*Assistant Examiner*—Carl H. Layno
*Attorney, Agent, or Firm*—Cecily Anne Snyder

[57] ABSTRACT

A method and circuit are described for automatically testing various components of a defibrillator at random or otherwise aperiodic time intervals. A random number is generated that falls within a range of numbers corresponding to minimum and maximum acceptable time intervals between successive testing of the defibrillator. Ambient conditions can be measured and the acceptable range of numbers adjusted accordingly. High energy test procedures may be performed less frequently, as appropriate for the measured ambient conditions. The range of numbers can also be adjusted to provide greater frequency testing where desirable, such as following a use of the defibrillator, following a repair of the defibrillator, to detect infant mortality effects, or to detect wear-out effects. The defibrillator includes a testing circuit for testing the various other components. The testing circuit includes a controller coupled with a timer, a random number generator, a memory, and an ambient condition sensor.

74 Claims, 4 Drawing Sheets

U.S. PATENT DOCUMENTS

| | | |
|---|---|---|
| 4,442,315 | 4/1984 | Segawa . |
| 4,488,555 | 12/1984 | Imran . |
| 4,494,552 | 1/1985 | Heath . |
| 4,504,773 | 3/1985 | Suzuki et al. . |
| 4,523,595 | 6/1985 | Zibell . |
| 4,539,995 | 9/1985 | Segawa . |
| 4,543,958 | 10/1985 | Cartmell . |
| 4,574,810 | 3/1986 | Lerman . |
| 4,583,549 | 4/1986 | Manoli . |
| 4,595,009 | 6/1986 | Leinders et al. . |
| 4,610,254 | 9/1986 | Morgan et al. . |
| 4,625,730 | 12/1986 | Fountain et al. . |
| 4,628,935 | 12/1986 | Jones et al. . |
| 4,733,670 | 3/1988 | Hays et al. . |
| 4,745,923 | 5/1988 | Winstrom . |
| 4,771,781 | 9/1988 | Lerman . |
| 4,785,812 | 11/1988 | Pihl et al. . |
| 4,852,572 | 8/1989 | Nakahashi et al. . |
| 4,895,169 | 1/1990 | Heath . |
| 4,957,109 | 9/1990 | Groeger et al. . |
| 5,078,134 | 1/1992 | Heilman et al. . |
| 5,080,099 | 1/1992 | Way et al. . |
| 5,097,830 | 3/1992 | Eikefjord et al. . |
| 5,099,844 | 3/1992 | Faupel . |
| 5,168,875 | 12/1992 | Mitchiner . |
| 5,184,620 | 2/1993 | Cudahy et al. . |
| 5,191,886 | 3/1993 | Paeth et al. . |
| 5,201,865 | 4/1993 | Kuehn . |
| 5,222,830 | 6/1993 | Morgan et al. . |
| 5,224,870 | 7/1993 | Weaver et al. . |
| 5,231,987 | 8/1993 | Robson . |
| 5,237,991 | 8/1993 | Baker, Jr. et al. . |
| 5,249,573 | 10/1993 | Fincke et al. . |
| 5,327,888 | 7/1994 | Imran . |
| 5,330,526 | 7/1994 | Fincke et al. . |
| 5,342,403 | 8/1994 | Powers et al. . |
| 5,400,782 | 3/1995 | Beaubiah . |
| 5,402,884 | 4/1995 | Gilman et al. . |
| 5,462,157 | 10/1995 | Freeman et al. . |
| 5,466,256 | 11/1995 | McAdams et al. . |
| 5,467,768 | 11/1995 | Suda et al. . |
| 5,549,646 | 8/1996 | Katz et al. .................................. 607/5 |
| 5,579,234 | 11/1996 | Wiley et al. . |
| 5,591,213 | 1/1997 | Morgan . |
| 5,607,454 | 3/1997 | Cameron et al. . |
| 5,645,571 | 7/1997 | Olson et al. . |

5,899,925

METHOD AND APPARATUS FOR APERIODIC SELF-TESTING OF A DEFIBRILLATOR

BACKGROUND OF THE INVENTION

1. Field of the Invention

This invention relates generally to a method and apparatus for automatic self-testing of electrical devices, and more particularly to a method and apparatus for automatic self-testing of electrical defibrillators.

2. Description of the Prior Art

Sudden cardiac death is the leading cause of death in the United States. Most sudden cardiac death is caused by ventricular fibrillation, in which the heart's muscle fibers contract without coordination, thereby interrupting normal blood flow to the body. The only known effective treatment for ventricular fibrillation is electrical defibrillation, in which an electrical pulse is applied to the patient's heart. The electrical pulse must be delivered within a short time after onset of ventricular fibrillation in order for the patient to have any reasonable chance of survival.

External defibrillators send electrical pulses to the patient's heart through electrodes applied to the patient's torso. External defibrillators are typically located and used in hospital emergency rooms, operating rooms, and emergency medical vehicles. Of the wide variety of external defibrillators currently available, automatic and semi-automatic external defibrillators ("AEDs") are becoming increasingly popular because they can be used by relatively inexperienced personnel. Such defibrillators are also especially lightweight, compact, and portable.

AEDs provide a number of advantages, including the availability of external defibrillation at locations where external defibrillation is not regularly expected, such as in residences, public buildings, businesses, personal vehicles, public transportation vehicles, etc. AEDs are typically subject to widely varying conditions and are used relatively infrequently, but are nevertheless expected to function reliably when used. Thus, regular testing of an AED is desirable, in order to sample readiness for use should it be needed. However, operators trained in the use of AEDs are usually inexperienced in the testing of medical equipment. Therefore, testing of AED functions is preferably performed automatically by the AED itself (known in the art as "self-testing"). Conventional self-testing systems for defibrillators test at regularly scheduled time intervals and/or in response to certain events, such as power-on events. As such, conditions potentially affecting certain defibrillator functions may not be adequately detected, and defibrillator reliability may then be compromised.

SUMMARY OF THE INVENTION

A method and circuit is provided for automatically and aperiodically testing a defibrillator. An aperiodic time interval is selected, and testing of the defibrillator is initiated after the aperiodic time interval has elapsed. Selecting an aperiodic time interval may include generating or otherwise selecting a random number and determining whether that random number falls within a given test interval range of numbers. Selecting an aperiodic time interval may also include measuring an ambient condition and then selecting a corresponding time interval. Selecting an aperiodic time interval may further include determining the age of the defibrillator, or whether the defibrillator was recently used or repaired, and then selecting a corresponding time interval. Initiating testing of the defibrillator may include selecting a test procedure and then determining whether that test procedure is one of a selected category of test procedures. If so, the test procedure is initiated at a frequency different from that associated with other test procedures.

In accordance with one embodiment of the present invention, a defibrillator includes a high voltage circuit, a controller, and a testing circuit. The high voltage circuit produces a high energy electrical pulse for delivery to a patient, and the controller is coupled with and controls the operations of the high voltage circuit. The testing circuit is coupled with and automatically tests the operations of the high voltage circuit at aperiodic time intervals. The defibrillator may also include an electrocardiogram ("ECG") circuit for detecting an electrocardiogram signal produced by the patient, in which case the testing circuit is also coupled with and automatically tests the operations of the ECG circuit at aperiodic time intervals. The testing circuit may include a timing circuit and a testing controller. The timing circuit produces a timing signal following elapse of a given time interval, and the testing controller receives the timing signal and initiates test procedures in response thereto. The testing circuit may also include a memory or a random number generator, each for providing values associated with aperiodic time intervals.

DESCRIPTION OF THE PREFERRED EMBODIMENTS

Currently available self-testing systems for defibrillators involve testing that is performed periodically. While such testing has the advantage of predictability, it includes the drawback that performance of defibrillator functions may themselves be affected periodically, and hence potentially not detected by periodic testing. For example, if automatic testing of a defibrillator occurs once a day, conditions such as a benign temperature or humidity environment may be present at the daily test time. Testing in synchronism with such conditions then fails to detect other conditions occurring at untested times of the day which may deleteriously affect defibrillator performance and reliability. Also, currently available self-testing systems do not modify test procedures or frequency to account for other conditions that might affect reliability-conditions such as defibrillator age, repair history, use history, etc.

One example defibrillator system is described in U.S. Pat. No. 5,607,454, entitled "Electrotherapy Method and Apparatus," the disclosure of which is incorporated herein by reference. Examples of defibrillators having automatic self-test features are described in U.S. Pat. No. 5,579,234, entitled "System for Automatically Testing an Electronic Device During Quiescent Periods," and in U.S. Pat. No. 5,591,213, entitled "Defibrillator System Condition Indicator," the disclosures of which are incorporated herein by reference.

In accordance with the present invention, a defibrillator is provided which includes a testing circuit for automatically and aperiodically testing defibrillator functions. Test frequency and procedures may also be modified to account for conditions potentially affecting defibrillator reliability and performance. In the following description, certain specific details are set forth in order to provide a thorough understanding of various embodiments of the present invention. It will be clear, however, to one skilled in the art that the present invention may be practiced without these details. In other instances, well-known circuits have not been shown in detail in order not to unnecessarily obscure the description of the various embodiments of the invention. Also not presented in any detail are those well-known control signals and signal timing protocols associated with the internal operation of defibrillators.

Figure 1:
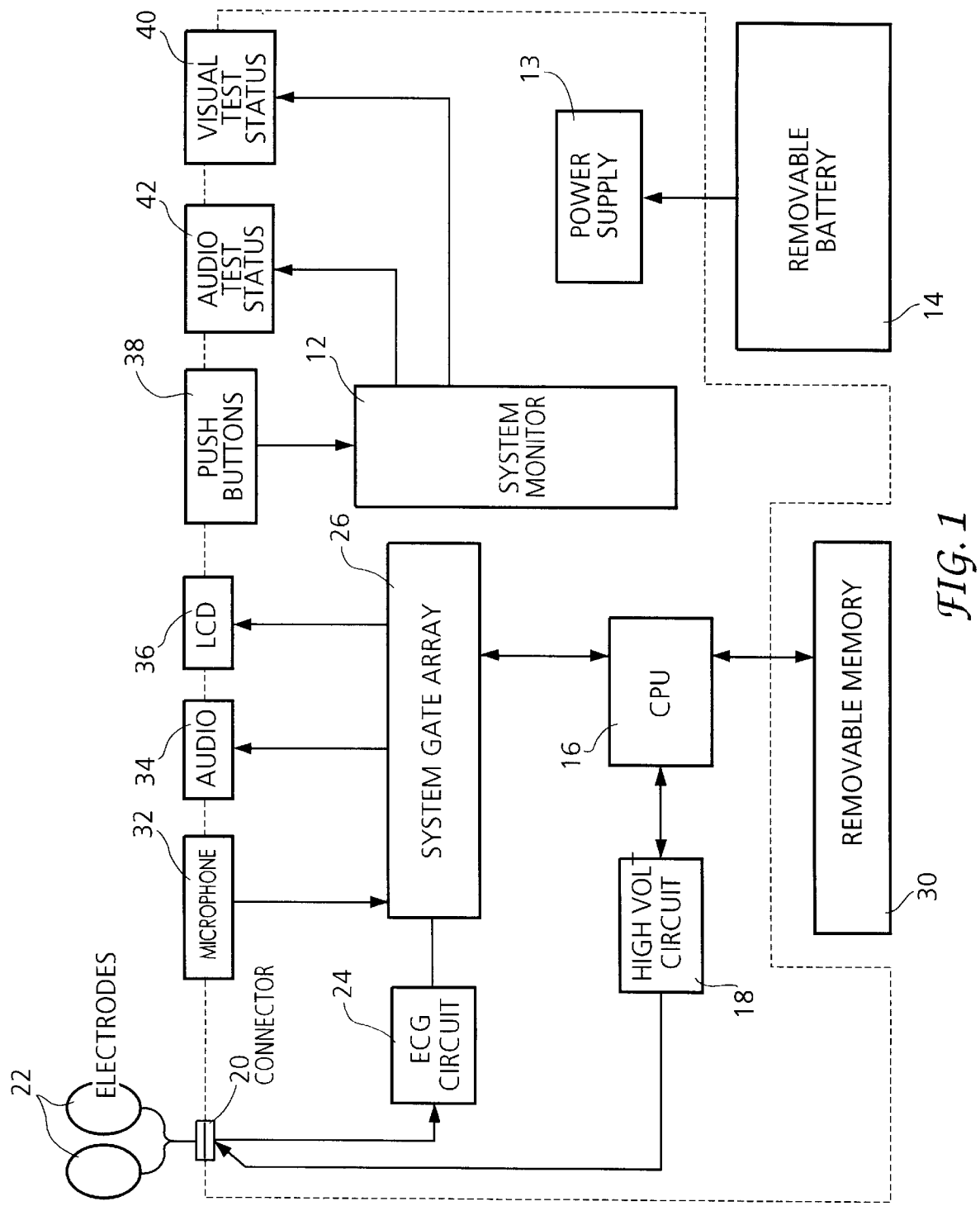
FIG. 1 is a functional block diagram depicting a defibrillator according to an embodiment of the present invention.

FIG. 1 is a functional block diagram depicting a defibrillator or AED 10 having a testing circuit or system monitor 12 in accordance with an embodiment of the present invention. The AED 10 includes a power supply 13, which is powered by an energy source such as a removable battery 14. A controller or central processing unit ("CPU") 16 controls the operation of the various components of the AED 10. A high voltage delivery circuit 18 delivers a pulse of electrical energy to an electrode connector or interface 20, and then to a patient via electrodes 22. The high voltage delivery circuit 18 typically includes a capacitor or a capacitor bank and appropriate switches (not shown), and delivery of the electrical pulse is controlled by the CPU 16.

An ECG circuit 24 acquires and processes the patient's ECG signals through the electrodes 22 and sends the signals to the CPU 16 via a system gate array 26. The system gate array 26 is a custom application specific integrated circuit ("ASIC") integrating many of the defibrillator's functions, such as display control and many of the instrument control functions. Providing the separate system gate array 26 allows the CPU 16 to focus on other tasks. Alternatively, the functionality of the system gate array 26 could be included within the operations performed by the CPU 16, or could be replaced by discrete logic circuit components or a separately dedicated CPU. The AED 10 also includes a memory device 30 (such as a removable personal computer memory card international association ["PCMCIA"] card or a magnetic tape), a microphone 32, an audio speaker 34, a liquid crystal display ("LCD") panel 36, and a set of push-button controls 38.

The system monitor 12 generates test signals at various times and in response to specified events, such as power-on events, to initiate testing of defibrillator functions. The system monitor 12 can also operate a fail-safe defibrillator status indicator, which includes a visual test status indicator 40 (which may be integrated within the LCD display 36) and an audio test status indicator 42 (which may be integrated within the audio speaker 34). The system monitor 12 applies test signals to the CPU 16 via a communication channel, and the CPU controls and gathers information from various tested defibrillator components via other communication channels, some of which pass through the system gate array 26.

Each of the various tested defibrillator components may itself contain circuitry (not shown) for testing and communicating component status to the CPU 16 and system monitor 12. For example, the ECG circuit 24 may include a signal generator for generating test ECG signals to test ECG amplifier and analog-to-digital converter functions, etc. As a further example, the high voltage delivery circuit 18 may include test load circuitry to which a high voltage pulse is delivered instead of to the electrode connector 20. Typically, the test load circuitry would include relay circuitry to isolate the high voltage delivery circuit 18 from the electrode connector 20 and apply the high voltage pulse to a test load impedance. Other components of the AED 10 may include similarly adapted circuitry for testing component function and communicating test results to the CPU 16 and the system monitor 12, as will be understood by those skilled in the art.

The functionality of the system monitor 12 could be included within the operations performed by the CPU 16. However, providing the separate system monitor 12 allows the CPU 16 to focus on other tasks. The testing circuit can also be conveniently powered separately from other components of the AED 10, resulting in energy savings. The system monitor 12 can then include its own separately dedicated power supply (not shown), which may be powered by the main battery 14 or by a separate dedicated battery (not shown).

Figure 2:
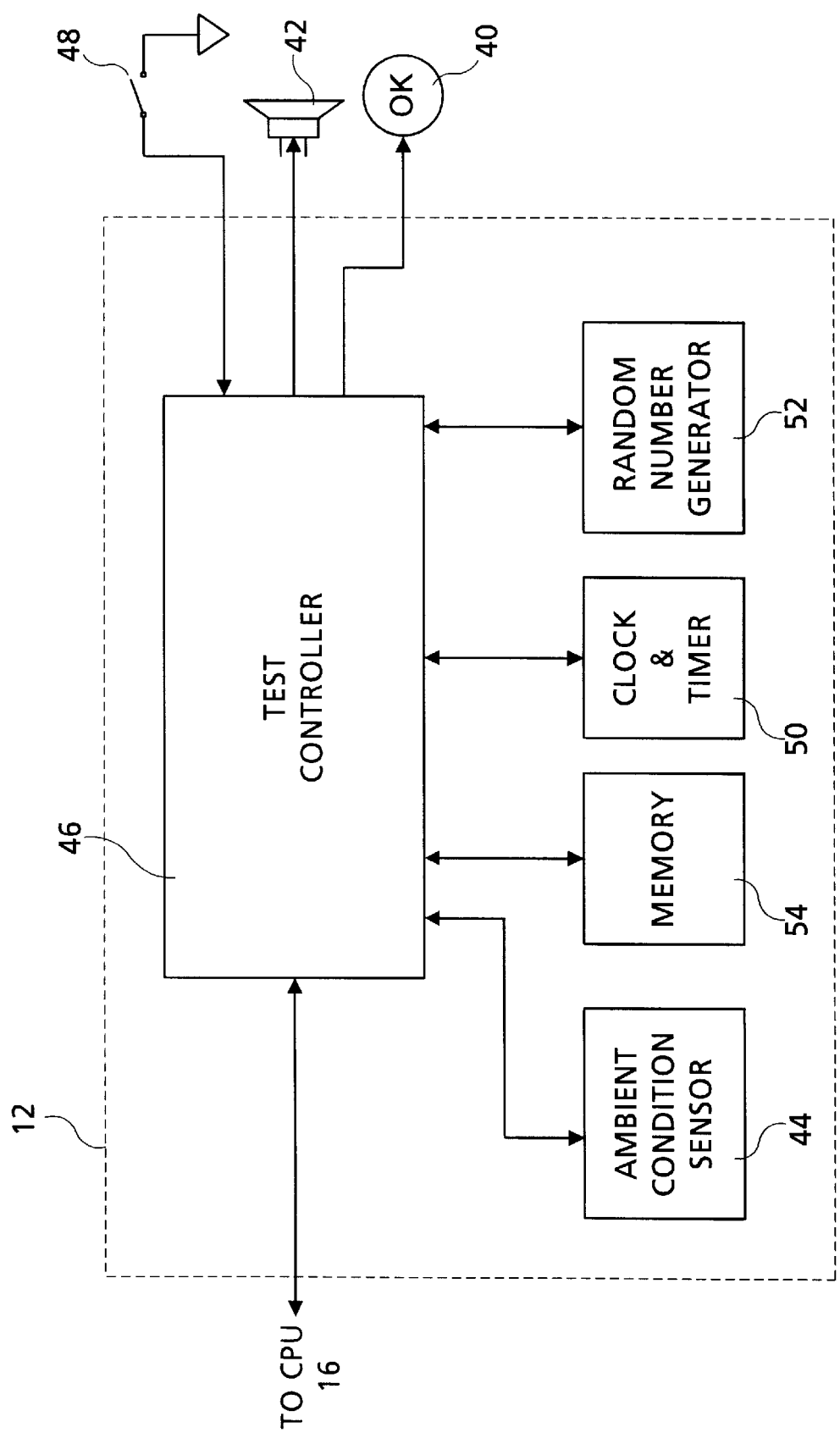
FIG. 2 is a functional block diagram depicting a system monitor included in the defibrillator of FIG. 1.

FIG. 2 is a functional block diagram depicting certain details of the system monitor 12. A test controller 46 executes primary functions of the system monitor 12. The test controller 46 may itself be a CPU or a microcontroller operating under software control, or may be a gate array ASIC or other suitably adapted circuitry. The test controller 46 controls operation of the visual and audible status indicators 40 and 42, and responds to power-on events, as depicted by the coupling with an on-button control 48.

An ambient condition sensor 44 is coupled with the test controller to provide signals corresponding to measured conditions such as temperature and humidity. A clock and timer circuit 50 is coupled with the test controller 46 to provide clock signal functionality to the test controller and to provide signals associated with the timing of certain events. A memory 54 is coupled with the test controller 46 to store data and instructions used by the test controller to execute test functions. A random number generator 52 is shown coupled with the test controller 46 to provide signals corresponding to random numbers, which may be used for loading random time values in the clock and timer circuit 50. Alternatively, time values may be stored or otherwise determined from data stored in the memory 54. Upon expiration of a given time interval, the clock and timer circuit 50 applies a control signal to the test controller 46 to initiate the various defibrillator self-test functions mediated by the test controller.

In accordance with an embodiment of the present invention, the system monitor 12 automatically tests defibrillator functions at random or otherwise aperiodic time intervals. The time intervals may be determined by the random number generator 52 providing signals for loading the timer circuit 50. The time intervals may be selected from a plurality of preprogrammed time values stored in the memory 54, with the selection of these values being random, sequential, etc. As a further alternative, the time intervals could be calculated or otherwise determined in accordance with any of a wide variety of non-periodic functions. Indeed, those skilled in the art will appreciate that any of numerous methods and suitably adapted circuitry may be employed for initiating defibrillator self-test functions at other than regular, periodic time intervals.

By initiating defibrillator self-test operations randomly or aperiodically, synchronism with periodically varying conditions, such as temperature and humidity, is avoided. Therefore, such aperiodic testing allows more accurate reliability testing than conventional periodic testing, which can inadvertently be synchronized with environmental conditions. Such aperiodic testing can also be advantageously tailored to change the type and frequency of the self-test performed. For example, high energy tests (such as a full energy defibrillator discharge test) need not be performed as frequently as low energy tests. Also, the mean frequency of the aperiodic testing can be modified depending on ambient or other conditions encountered upon "wake-up" of the AED 10 for testing.

Generally an electronic device, such as the AED 10, is likely to fail or perform poorly when something unusual happens to it. In the case of an AED, its use is something unusual-such devices being designed to spend most of their service lives not being used. During a use, the AED 10 may be dropped or exposed to wet conditions, and the battery 14 (see FIG. 1) suffers some depletion. Following such a use, near-term effects such as mechanical fatigue of circuit connections or corrosion may adversely impact defibrillator performance and reliability. Also, the battery 14 may be substantially depleted, although not quite reaching a low battery condition status. Consequently, the AED 10 is more likely to fail when being used, or soon thereafter, than when remaining in a standby condition for an extended period of time.

In accordance with an embodiment of the present invention, the system monitor 12 adjusts the mean frequency of the aperiodic testing to provide more frequent testing following the use of the AED 10. Such testing more effectively identifies failures precipitated by conditions during the use of the AED 10. The time intervals separating defibrillator self-test operations are made gradually larger as increasing numbers of tests are passed successfully, since a determination of consistently stable defibrillator functions justifies increasing the time intervals between successive tests of those functions. The time interval spacing may, for example, follow a logarithmic progression until normal standby test intervals are warranted.

The repair of the AED 10 might also warrant more frequent initial testing. Similarly, more frequent testing can be performed soon after manufacture of the AED 10, to more rapidly identify any "infant mortality" effects. Later in the life of the AED 10 (as a function of time from manufacture, number of shocks delivered, use history, repair history, etc.), the frequency of testing can gradually increase to identify wear-out failures more quickly.

Depending on the use or other conditions experienced by the AED 10, some test procedures may be performed more frequently than others. For example, cold temperatures adversely affect battery performance, but do not otherwise normally affect many of the other defibrillator components. If the temperature tends to be cold upon wake-ups, the mean interval of high energy testing can be extended in order to minimize battery drain. If, however, high humidity is detected, high energy testing can be performed more frequently to determine if the humidity is adversely affecting high voltage performance. As a further example, the frequency of battery testing may be adjusted as a function of the battery's age and/or history of use of the battery in AED 10. In later battery life, increasingly frequent testing will tend to decrease the exposure to any marginal battery conditions while the AED 10 is in standby mode. As the battery begins to reach a depletion stage, increasingly frequent testing will itself accelerate the depletion of the battery, thereby accelerating the needed replacement of the battery.

Such aperiodic testing achieves a number of important advantages. Failures precipitated by use of the AED 10 are detected sooner. The mean energy required for testing can, in the long run, be less than that required for traditional periodic testing methods, resulting in improved battery life. It is also possible that a data trend analysis of variables measured during post-use testing can be predictive of failure, thereby allowing the AED 10 to be repaired prior to an actual failure. Those skilled in the art will also appreciate further advantages achievable by the above-described aperiodic testing.

Figure 3:
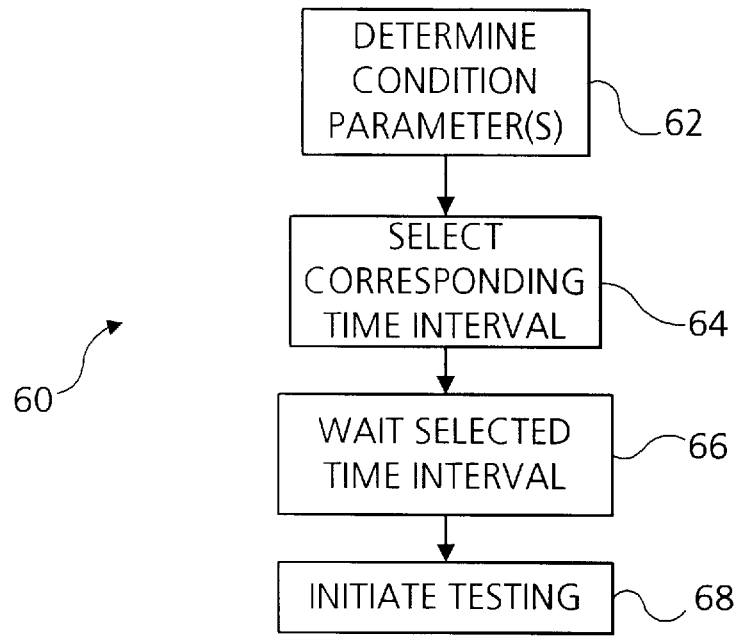
FIG. 3 is a flowchart depicting a method of aperiodically initiating self-testing of the defibrillator of FIG. 1.

FIG. 3 is a flow chart depicting a method 60 of aperiodically initiating selftesting of the AED 10. In step 62, one or more condition parameters are determined. Example condition parameters include ambient conditions such as temperature and humidity, the number of uses of the AED 10 and/or the time since the last such use, the age of the AED 10 or the battery's state of change (as a function of time from manufacture, number of shocks delivered, use history, etc.), parameters relating to the repair and/or component replacement, etc. In step 64, a time interval corresponding to the determined condition parameter(s) is selected. Following elapse of the time interval (depicted as a wait state 66), defibrillator self-test operations are initiated in step 68.

The determination of various condition parameters can be accomplished in any number of ways. Of course, determining ambient conditions, such as temperature and humidity, is most conveniently done by measuring such conditions with the sensor 44 (see FIG. 2). The time elapsed since a most recent use of the AED 10 may be provided by the clock and timer circuit 50, or may be determined from data stored in the memory 54. Parameters associated with the repair history, use history, and age of the AED 10 (whether old or young) can also be determined from data stored in the memory 54 data which is updated according to the occurrence of events pertinent to such condition parameters, as will be clear to those skilled in the art. The battery's state of change can be determined by measuring the battery's terminal voltage and the battery's response under load.

Figure 4:
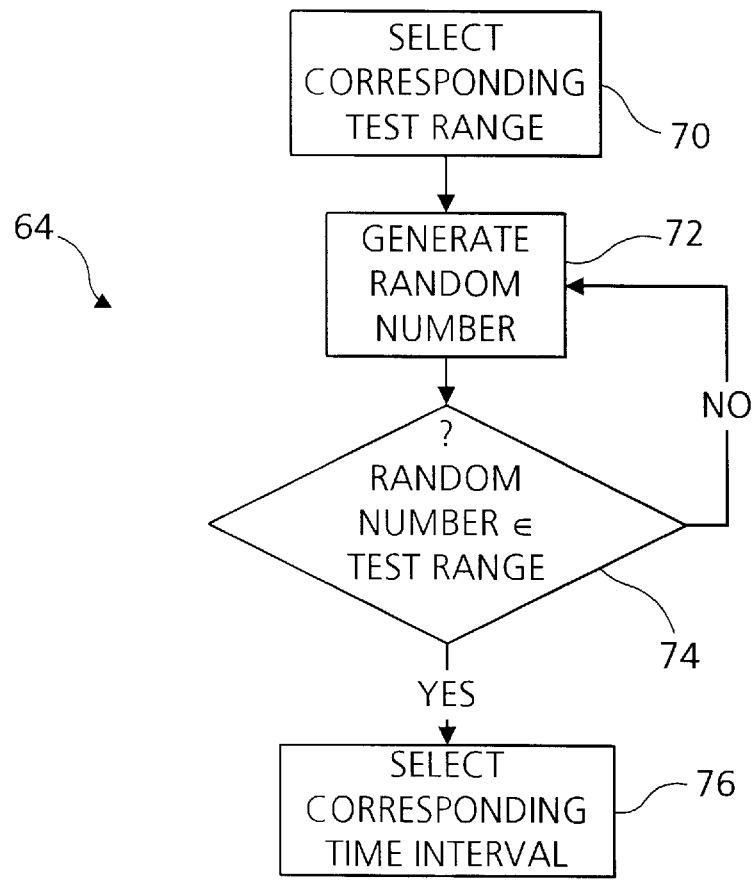
FIG. 4 is a flowchart depicting a method of selecting time intervals in the method of FIG. 3.

The time interval corresponding to the determined condition parameter(s) can be selected or otherwise determined according to any of a wide variety of methods consistent with the above description of varying the frequency of defibrillator testing. FIG. 4 is a flow chart depicting one such method 64. In step 70, a test interval or range of values is selected in correspondence with the determined condition parameter(s). This test interval may represent a range of values corresponding to an acceptable range of time intervals between successive testing of defibrillator functions, given the determined condition parameter(s), as will be understood by those skilled in the art. Following a use of the AED 10, for example, successive test interval means may follow a roughly logarithmic progression until normal standby testing is again warranted.

A random number is then generated in step 72, and a conditional branch step 74 is performed, in which the generated random number is compared to the test interval. If the random number is not an element of the test interval, the method returns to step 72, in which another random number is generated. If, instead, the random number is an element of the test interval, a time interval is selected corresponding to that random number in step 76. The time interval may simply be equal to the random number, or may be correspondingly calculated, selected graphically or from a look-up table, etc.

Those skilled in the art will appreciate that the process flow depicted in FIGS. 3 and 4 is just one of many methods of initiating defibrillator self-test operations at aperiodic time intervals. The selection and order of certain steps can be readily modified, with some steps omitted and others added. Any of a number of suitable methods may be employed to select a random time interval, whether selected in correspondence with particular condition parameters or not. Also, selecting a random time interval is just one example of, more generally, selecting or otherwise determining a time interval that is not regular or periodic.

The particular process flow depicted in FIGS. 3 and 4 combines self-testing of defibrillator functions at random time intervals with self-testing at frequencies dictated by the determined condition parameter(s). Those skilled in the art will appreciate, however, that the scope of the present invention also includes solely testing at random or otherwise aperiodic time intervals, as well as solely testing at frequencies adjusted in accordance with determined condition parameters.

Figure 5:
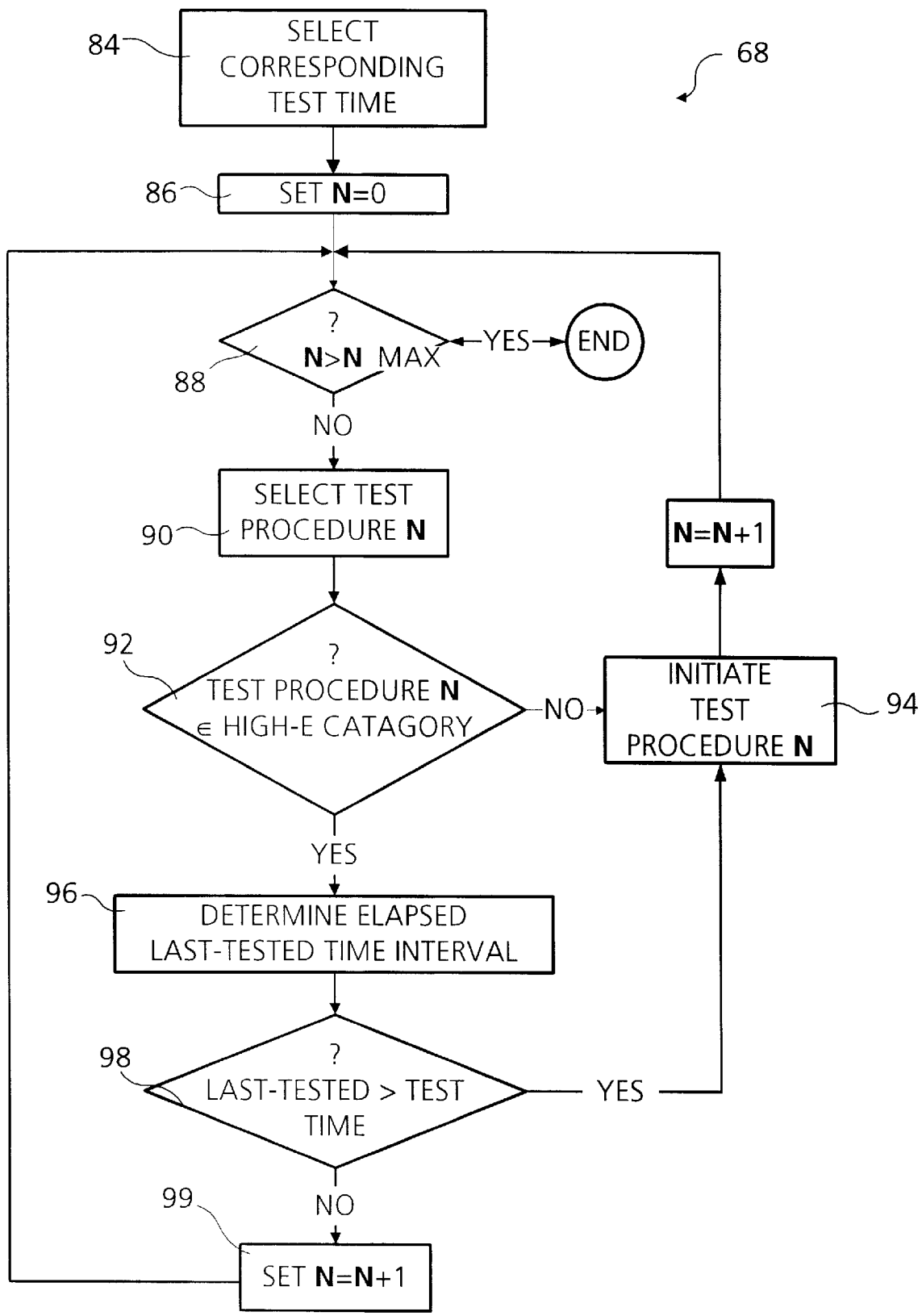
FIG. 5 is a flowchart depicting a method of selecting test procedures to be initiated in the method of FIG. 3.

As described above, not all test procedures need be performed each time the AED 10 is tested. Therefore, the step 68 depicted in FIG. 3 can include the determination of which test procedure should be performed. Any of a number of acceptable methods can be employed for such a determination. One such method 68 is shown in FIG. 5. In step 84, a test time value is selected or otherwise determined corresponding to the condition parameter(s) determined in step 62 of FIG. 3. The test time value may represent a minimum acceptable time interval between successive performance of a particular category of test procedures, given the determined condition parameter(s), as will be understood by those skilled in the art. An integral value N is set to zero in step 86 and compared to a maximum value $N_{MAX}$ in a conditional branch step 88. The value $N_{MAX}$ reflects the number of distinct test procedures that can be performed during defibrillator self-test operations. If the value N exceeds $N_{MAX}$, then defibrillator self-testing operations are concluded. Otherwise, a test procedure corresponding to the value N is selected in step 90.

A conditional branch step 92 determines whether the selected test procedure is an element of a selected category of test procedures, such as high energy tests. If not, the test procedure is performed in step 94. If, however, the selected test procedure is of the selected category, a determination of a last-tested time interval (the time elapsed since a most recent performance of the test procedure) is determined in step 96. A conditional branch step 98 is then performed in which the last-tested time interval is compared to the previously selected test time value. If the last-tested time interval exceeds the test time value, performance of the selected test procedure is initiated in step 94. If, however, the last-tested time value does not exceed the selected test time, the value N is incremented by 1 in step 99, and the sequence of operations branches back to conditional branch step 88, in which the value N is compared to the maximum value $N_{MAX}$.

Those skilled in the art will appreciate that the process flow depicted in FIG. 5 is just one of many methods of adjusting the frequency of defibrillator self-test operations for certain selected test procedures. The selection and order of certain steps can be readily modified, with some steps omitted and others added. Any of a number of suitable methods may be employed to appropriately adjust the frequency of selected test procedures, whether adjusted in correspondence with particular condition parameters or not. The method depicted in FIG. 5 selectively initiates test procedures depending on whether or not they belong to a single selected category. However, those skilled in the art will appreciate that this method can be readily adapted to identify and initiate test 10 procedures according to multiple categories.

Each of the circuits whose function and interconnection is described in connection with FIGS. 1 and 2 is of a type known in the art, and one skilled in the art would be able to use such circuits in the described combination to practice the present invention. The internal details of these particular circuits are not part of, nor critical to, the invention. Therefore, a detailed description of the internal circuit operation is not required. Similarly, each of the steps depicted in FIGS. 3–5 is of a type well known in the art and may itself include a sequence of operations which need not be described herein.

It will be appreciated that, although specific embodiments of the invention have been described herein for purposes of illustration, various modifications may be made without deviating from the spirit and scope of the invention. Those skilled in the art will appreciate that a number of suitable circuits, other than those particular ones described above, can be adapted to implement an aperiodic self-testing defibrillator. For example, any of a number of memory devices may be employed for storing data used to initiate defibrillator self-test operations. The memory functionality may itself be integrated into other circuits, as could the timing/clock circuitry and the random number generation. Those skilled in the art will also appreciate that a number of suitable methods, other than the particular ones described above, may be employed for aperiodically initiating defibrillator self-test operations. Accordingly, the invention is not limited except as by the appended claims.

What is claimed is:

1. A method of automatically testing a defibrillator, comprising the steps of:

selecting an aperiodic time interval; and initiating testing of the defibrillator after the aperiodic time interval has elapsed.

2. The method of claim 1 wherein the step of selecting an aperiodic time interval includes the step of selecting a random time interval.

3. The method of claim 1 wherein the step of selecting an aperiodic time interval includes the step of selecting one of a plurality of predetermined time intervals.

4. The method of claim 1 wherein the step of selecting an aperiodic time interval includes the step of generating a random number, the aperiodic time interval being determined as a function of the random number.

5. The method of claim 1 wherein the step of selecting an aperiodic time interval includes the steps of:

generating a first random number;

determining whether the first random number falls within a test interval range of numbers; and if the first random number does not fall within the test interval range, generating a second random number.

6. The method of claim 1 wherein the step of selecting an aperiodic time interval includes the steps of:

determining a condition parameter; and selecting an aperiodic time interval corresponding to the determined condition parameter.

7. The method of claim 6 wherein the step of determining a condition parameter includes the step of measuring an ambient temperature or an ambient humidity.

8. The method of claim 6 wherein the step of determining a condition parameter includes the step of determining a time associated with a most recent use of the defibrillator.

9. The method of claim 6 wherein the step of determining a condition parameter includes the step of determining a time associated with a most recent repair of the defibrillator.

10. The method of claim 6 wherein the step of determining a condition parameter includes the step of determining a time associated with an age of the defibrillator.

11. The method of claim 1 wherein the step of initiating testing of the defibrillator includes the steps of:
   selecting a test procedure;
   determining whether the test procedure is one of a selected category of test procedures;
   if the test procedure is one of the selected category, then determining an elapsed last-tested time interval since a most recent completion of the test procedure;
   comparing the last-tested time interval to a selected test time value; and
   if the last-tested time interval exceeds the test time value, then initiating the test procedure.

12. The method of claim 11 wherein the step of determining whether the test procedure is one of a selected category of test procedures includes the step of determining whether the test procedure is one of a high-energy category of test procedures.

13. The method of claim 11 wherein the test time value is selected by determining a condition parameter and determining a time value corresponding to the condition parameter.

14. The method of claim 13 wherein determining a condition parameter includes measuring an ambient temperature or an ambient humidity.

15. The method of claim 13 wherein determining the condition parameter includes determining a time associated with a most recent use of the defibrillator.

16. The method of claim 13 wherein determining the condition parameter includes determining a time associated with a most recent repair of the defibrillator.

17. The method of claim 13 wherein determining the condition parameter includes determining a time associated with an age of the defibrillator.

18. A method of automatically testing a defibrillator, comprising:
   determining if the defibrillator is subject to a selected condition;
   if the defibrillator is subject to the selected condition, then initiating testing of the defibrillator at a first interval; and
   if the defibrillator is not subject to the selected condition, then initiating testing of the defibrillator at a second interval.

19. The method of claim 18 wherein the step of determining if the defibrillator is subject to a selected condition includes the step of determining if the defibrillator was recently used.

20. The method of claim 18 wherein the step of determining if the defibrillator is subject to a selected condition includes the step of determining if the defibrillator was recently repaired.

21. The method of claim 18 wherein the step of determining if the defibrillator is subject to a selected condition includes the step of determining if the defibrillator is of young age.

22. The method of claim 18 wherein the step of determining if the defibrillator was subject to a selected condition includes the step of determining if the defibrillator is of old age.

23. The method of claim 18 wherein the step of determining if the defibrillator is subject to a selected condition includes the step of determining if the defibrillator was recently used, and wherein the first interval is progressively varied from a higher to a lower interval.

24. The method of claim 18 wherein the step of determining if the defibrililator is subject to a selected condition includes the step of determining if the defibrillator was recently repaired, and wherein the first interval is progressively varied from a higher to a lower frequency.

25. The method of claim 18 wherein the step of determining if the defibrillator is subject to a selected condition includes the step of determining if the defibrillator is of young age, and wherein the first interval is progressively varied from a higher to a lower frequency.

26. The method of claim 18 wherein the step of determining if the defibrillator is subject to a selected condition includes the step of determining if the defibrillator is of old age, and wherein the first interval is progressively varied from a lower to a higher frequency.

27. The method of claim 18 wherein the second interval is a constant frequency.

28. A method of automatically testing a defibrillator, comprising the steps of:
   determining a defibrillator condition;
   selecting a time interval corresponding to the condition; and
   testing the defibrillator after the selected time interval has elapsed.

29. The method of claim 28 wherein the step of determining a defibrillator condition includes the step of determining an ambient condition.

30. The method of claim 28 wherein the step of determining a defibrillator condition includes the step of determining an age of the defibrillator.

31. The method of claim 28 wherein the step of determining a defibrillator condition includes the step of determining a use history of the defibrillator.

32. The method of claim 28 wherein the step of determining a defibrillator condition includes the step of determining a repair history of the defibrillator.

33. The method of claim 28 wherein the step of selecting a time interval corresponding to the condition includes the steps of:
   selecting a range of numbers corresponding to the condition; and
   generating a random number that falls within the selected range.

34. The method of claim 33 wherein the step of selecting a range of numbers includes the step of selecting a number corresponding to a minimum acceptable time interval between successive testing of the defibrillator.

35. The method of claim 33 wherein the step of selecting a range of numbers includes the step of selecting a number corresponding to a maximum acceptable time interval between successive testing of the defibrillator.

36. The method of claim 33 wherein the step of generating a random number that falls within the selected range includes the steps of:
   generating a first random number;
   determining whether the first random number falls within the selected range; and
   if the first random number does not fall within the selected range, generating additional random numbers until one is determined to fall within the selected range.

37. The method of claim 33 wherein the step of selecting a time interval corresponding to the random number includes the step of selecting a time interval equal to the random number.

38. A method of automatically testing a defibrillator, comprising the steps of:
   selecting a test procedure;
   determining whether the test procedure is one of a selected category of test procedures; and if the test procedure is one of the selected category, then:
  determining an elapsed time interval since a most recent performing of the test procedure;
  comparing the elapsed time interval to a predetermined test time value; and
  if the elapsed time interval exceeds the test time value, then performing the test procedure.

39. The method of claim 38 wherein the test time value is determined by determining a minimum acceptable time interval between successive performances of the selected category of test procedures.

40. The method of claim 38 wherein the test time value is determined by determining a defibrillator condition and selecting a time value corresponding to the defibrillator condition.

41. The method of claim 40 wherein determining the defibrillator condition includes measuring ambient temperature or ambient humidity.

42. The method of claim 40 wherein determining the defibrillator condition includes determining a time associated with a most recent use of the defibrillator.

43. The method of claim 40 wherein determining the defibrillator condition includes determining a time associated with a most recent repair of the defibrillator.

44. The method of claim 40 wherein determining the defibrillator condition includes determining an age of the defibrillator.

45. The method of claim 40 wherein selecting a time value corresponding to the defibrillator condition includes selecting a minimum acceptable time interval, in correspondence with the defibrillator condition, between successive performances of the selected category of test procedures.

46. The method of claim 38 wherein the step of determining whether the test procedure is one of a selected category of test procedures includes the step of determining whether the test procedure is one of a high energy category of test procedures.

47. An electrical defibrillator, comprising a testing circuit operable to automatically test other components of the electrical defibrillator at aperiodic time intervals.

48. The electrical defibrillator of claim 47 wherein the testing circuit is operable to determine an ambient condition and to correspondingly adjust the aperiodic time intervals.

49. The electrical defibrillator of claim 47 wherein the testing circuit is operable to determine a use history of the defibrillator and to correspondingly adjust the aperiodic time intervals.

50. The electrical defibrillator of claim 47 wherein the testing circuit is operable to determine a repair history of the defibrillator and to correspondingly adjust the aperiodic time intervals.

51. The electrical defibrillator of claim 47 wherein the testing circuit is operable to determine an age of the defibrillator and to correspondingly adjust the aperiodic time intervals.

52. The electrical defibrillator of claim 47 wherein the testing circuit is operable to perform a first category of selected tests less frequently than a second category of selected tests.

53. The electrical defibrillator of claim 47 wherein the testing circuit is operable to determine an ambient condition and to correspondingly perform a first category of selected tests more frequently than a second category of selected tests.

54. The electrical defibrillator of claim 47 wherein the testing circuit is operable to determine a use history of the defibrillator and to correspondingly perform a first category of selected tests more frequently than a second category of selected tests.

55. The electrical defibrillator of claim 47 wherein the testing circuit is operable to determine a repair history of the defibrillator and to correspondingly perform a first category of selected tests more frequently than a second category of selected tests.

56. The electrical defibrillator of claim 47 wherein the testing circuit is operable to determine an age of the defibrillator and to correspondingly perform a first category of selected tests more frequently than a second category of selected tests.

57. The electrical defibrillator of claim 47 wherein the testing circuit includes:
  a timing circuit operable to produce a timing signal following elapse of an aperiodic time interval; and
  a controller circuit coupled with the timing circuit and operable to receive the timing signal and to initiate testing of the other components in response thereto.

58. The electrical defibrillator of claim 47 wherein the testing circuit includes:
  a random number generator operable to produce a random number;
  a timing circuit coupled with the random number generator and operable to produce a timing signal following elapse of a time interval corresponding with the random number; and
  a controller circuit coupled with the timing circuit and operable to receive the timing signal and to initiate testing of the other components in response thereto.

59. The electrical defibrillator of claim 47 wherein the testing circuit includes:
  a memory operable to store data;
  a timing circuit coupled with the memory and operable to produce a timing signal following elapse of a time interval corresponding with the data stored in the memory; and
  a controller circuit coupled with the timing circuit and operable to receive the timing signal and to initiate testing of the other components in response thereto.

60. The electrical defibrillator of claim 47 wherein the testing circuit includes:
  a sensor operable to measure an ambient condition value;
  a timing circuit coupled with the sensor and operable to produce a timing signal following elapse of an aperiodic time interval corresponding with the measured ambient condition value; and
  a controller coupled with the timing circuit and operable to receive the timing signal and to initiate testing of the other components in response thereto.

61. An electrical defibrillator for defibrillating a patient, comprising:
  a high voltage circuit operable to produce a high energy electrical pulse for delivery to the patient;
  a controller circuit coupled with and operable to control operations of the high voltage circuit; and
  a testing circuit coupled with and operable to test operations of the high voltage circuit at aperiodic time intervals.

62. An electrical defibrillator for defibrillating a patient, comprising:
  a high voltage circuit operable to produce a high energy electrical pulse for delivery to the patient;
  a controller circuit coupled with and operable to control operations of the high voltage circuit; and
  a testing circuit coupled with and operable to test operations of the high voltage circuit at aperiodic time intervals wherein the testing circuit is coupled with the high voltage circuit by the controller circuit.

63. The electrical defibrillator of claim 61 wherein the testing circuit includes a random number generator operable to generate random numbers, the testing circuit being operable to test operations of the high voltage circuit at time intervals corresponding thereto.

64. The electrical defibrillator of claim 61 wherein the testing circuit includes a sensor operable to determine an ambient condition value, the testing circuit being operable to test operations of the high voltage circuit at time intervals corresponding thereto.

65. The electrical defibrillator of claim 61 wherein the testing circuit includes a memory adapted to store data corresponding to a use history of the defibrillator, the testing circuit being operable to test operations of the high voltage circuit at time intervals corresponding thereto.

66. The electrical defibrillator of claim 61 wherein the testing circuit includes a memory adapted to store data corresponding to a repair history of the defibrillator, the testing circuit being operable to test operations of the high voltage circuit at time intervals corresponding thereto.

67. The electrical defibrillator of claim 61 wherein the testing circuit includes a memory adapted to store data corresponding to an age of the defibrillator, the testing circuit being operable to test operations of the high voltage circuit at time intervals corresponding thereto.

68. The electrical defibrillator of claim 61, further comprising an ECG circuit adapted to detect an electrocardiogram signal produced by the patient, the controller circuit coupled with and operable to control operations of the ECG circuit, and the testing circuit coupled with and operable to test operations of the ECG circuit at aperiodic time intervals.

69. An electrical defibrillator for defibrillating a patient, comprising:

a high voltage circuit operable to produce a high energy electrical pulse for delivery to the patient;

a controller circuit coupled with and operable to control operations of the high voltage circuit;

a testing circuit coupled with and operable to test operations of the high voltage circuit at aperiodic time intervals; and an ECG circuit adapted to detect an electrocardiogram signal produced by the patient, the controller circuit coupled with and operable to control operations of the ECG circuit, and the testing circuit coupled with and operable to test operations of the ECG circuit at aperiodic time intervals wherein the testing circuit is coupled with the ECG circuit by the controller circuit.

70. The electrical defibrillator of claim 68 wherein the testing circuit is operable to test operations of the high voltage circuit less frequently than operations of the ECG circuit.

71. The electrical defibrillator of claim 68 wherein the testing circuit includes a sensor operable to determine an ambient condition value, the testing circuit being operable to test operations of the ECG circuit at time intervals corresponding thereto.

72. The electrical defibrillator of claim 68 wherein the testing circuit includes a memory operable to store data corresponding to a use history of the defibrillator, the testing circuit being operable to test operations of the ECG circuit at time intervals corresponding thereto.

73. The electrical defibrillator of claim 68 wherein the testing circuit includes a memory operable to store data corresponding to a repair history of the defibrillator, the testing circuit being operable to test operations of the ECG circuit at time intervals corresponding thereto.

74. The electrical defibrillator of claim 68 wherein the testing circuit includes a memory operable to store data corresponding to an age of the defibrillator, the testing circuit being operable to test operations of the ECG circuit at time intervals corresponding thereto.

\* \* \* \* \*